United States Patent [19]

Hudkins et al.

[11] Patent Number: 5,801,190
[45] Date of Patent: Sep. 1, 1998

[54] FUSED PYRROLO[2,3-C] CARBAZOLE-6-ONES

[75] Inventors: Robert L. Hudkins, Chester Springs; James L. Diebold, Norristown, both of Pa.; Ernest Knight, Jr., Wilmington, Del.

[73] Assignee: Cephalon, Inc., West Chester, Pa.

[21] Appl. No.: 827,215

[22] Filed: Mar. 28, 1997

Related U.S. Application Data

[63] Continuation of Ser. No. 604,474, Feb. 21, 1996, Pat. No. 5,616,724.

[51] Int. Cl.$^6$ ............ A61K 31/40; C07D 487/04; C07D 487/14
[52] U.S. Cl. ............ 514/410; 548/416; 548/417
[58] Field of Search ............ 514/410; 548/416, 548/417

[56] References Cited

U.S. PATENT DOCUMENTS

| | | | |
|---|---|---|---|
| 4,552,842 | 11/1985 | Nettleton, Jr. et al. | 435/75 |
| 4,912,107 | 3/1990 | Kleinschroth et al. | 514/232.5 |
| 4,923,986 | 5/1990 | Murakata et al. | 540/545 |
| 5,057,614 | 10/1991 | Davis et al. | 548/466 |
| 5,185,260 | 2/1993 | Crissman et al. | 435/244 |
| 5,405,864 | 4/1995 | Broka | 514/415 |

FOREIGN PATENT DOCUMENTS

| | | |
|---|---|---|
| 0 370 236 | 5/1990 | European Pat. Off. |
| 0 384 349 | 8/1990 | European Pat. Off. |
| 0 434 057 | 6/1992 | European Pat. Off. ...... C07D 487/14 |
| 0 545 195 A1 | 6/1993 | European Pat. Off. |
| 0 558 962 A1 | 9/1993 | European Pat. Off. |
| WO 91 09127 | 6/1991 | WIPO ...... C12N 15/38 |

OTHER PUBLICATIONS

Moody et al., J. Org. Chem., 1992, 57, 2105.
Bergman et al, "Coupling of Indoleacetic Acid Trianion or Methyl Indoleacetic Acid Dianion. A Biomimetic Approach to Indolocarbazole Alkaloids," *Tetrahedron Letters*, vol. 28, No. 38, pp. 4441–4444 (1987).
Bit et al., "Inhibitors of Protein Kinase C. 3. Potent and Highly Selective Bisindolylmaleimides by Conformational Restriction," *J. Med. Chem.* 36:21–29 (1993).
Bozyczko–Coyne et al., "A rapid fluoremetric assay to measure neuronal survival in vitro," *Journal of Neuroscience Methods* 50:205–216 (1993).
Brenner et al., "Synthesis of Arcyriarubin B and Related Bisindolylamleimides," *Tetrahedron* 44:2887–2892 (1988).
Buu–Hol et al., "Carcinogenic Nitrogen Compounds," *J. Che. Soc.* (1956) 1515–1518.
Davis et al., "Potent selective inhibitors of protein kinase C," *FEBS Letters*, vol. 259, No. 1, pp. 61–63 (1989).
Davis et al., "A Convenient Synthesis of Bisindolyl–and Indolylaryl–Maleic Anhydrides," *Terahedron Letters*, vol. 31, No. 16, pp. 2453–2356 (1990).

Davis et al., "A Mild Conversion of Maleic Anhydrides into Maleimides," *Tetrahedron Letters*, vol. 31, No. 36, pp. 5201–5204 (1990).
Davis et al., "Inhibitors of Protein Kinase C. 1. 1 2,3–Bisarylamaleimides," *J. Med. Chem.* 35:177–184 (1992).
Davis et al., "Inhibitors of Protein Kinase C. 2. Substituted Bisindolylmaleimides with Improved Potency and Selectivity," *J. Med. Chem.* 35:994–1001 (1992).
Davis et al., "The Design of Inhibitors of Protein Kinase C; The Solution Conformation of Staurosporine," *J. Chem. Soc., Chem. Commun.* p. 182–184 (1991).
Fraser, "Expression of Eucaryotic Genes in Insect Cell Cultures," *In Vitro Cellular & Developmental Biology* (1989) 25:225–235.
Gallant et al., "A Stereoselective Synthesis of Indol–β–N–glycosides: An Application to the Synthesis of Rebeccamycin," *J. Org. Chem.* 58:343–349 (1993).
Hallböök, et al., Evolutionary Studies of the Nerve Growth Factor Family Reveal a Novel Member Abundantly Expressed in Xenopus Ovary, *Neuron,* (1991) 6:845–858.
Hara et al., Staurosporine, a Novel Protein Kinase C Inhibitor, Prevents Postischemic Neuronal Damage in the Gerbil and Rat, *Journal of Cerebral Blood Flow and Metabolism* (1990) 10:646–653.

(List continued on next page.)

*Primary Examiner*—Johann Richter
*Assistant Examiner*—Laura L. Stockton
*Attorney, Agent, or Firm*—Fish & Richardson P.C.

[57] ABSTRACT

Disclosed in this patent document are synthetic, biologically active molecules referred to as fused pyrrolo[2,3-c] carbazole-6-ones. These molecules are represented by the following general formulae:

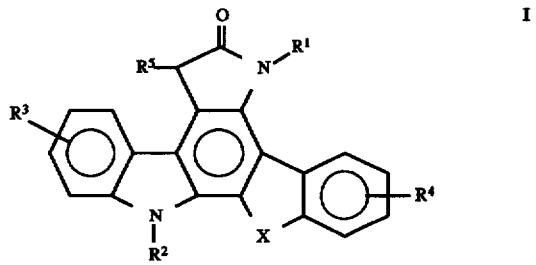

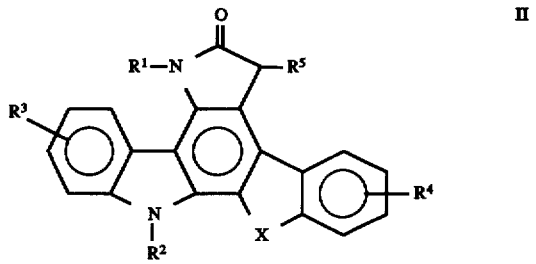

Methods for making and using the fused pyrrolo[2,3-c] carbazole-6-ones are also disclosed.

27 Claims, 5 Drawing Sheets

OTHER PUBLICATIONS

Hendricks et al., "2-Aryl-Indolyl Maleimides-Novel and Potent Inhibitors of Protein Kinase C," *Biorganic & Medicinal Chemistry Letters*, vol. 5, No. 1, pp. 67-72 (1995).

Hughes et al., "Synthesis of Arcyriaflavin B," *Tetrahedron Letters*, vol. 24, No. 13, pp. 1441-1444 (1983).

Hughes et al., "Synthesis of the Indol[2,3-a]carbazole Natural Products Staurosporinone and Arcyriaflavin B," *J. Chem. Soc. Perkin Trans. 1* pp. 2475-2480 (1990).

Kamiya Biomedical Co., Product List (1993).

Kaneko et al., "Two Synthetic Approaches to Rebeccamycin," *Tetrahedron Letters*, vol. 26, No. 34, pp. 4015-4018 (1985).

Kikkawa et al., Calcium-activated, Phospholipid-dependant Protein Kinase from Rat Brain, *The Journal of Biological Chemistry* (1982) 257:13341-13348.

Link et al., "The First Synthesis of a Fully Functionalized Core Structure of Staurosporine: Sequential Indolyl Glycosidation by Endo and Exo Glycals," *J. Am. Chem. Soc.* 115:3782-3783 (1993).

Magnus et al., "Indole-2,3-Quinodimethanes," *Tetrahedron*, vol. 40, No. 14, pp. 2795-2797 (1984).

Meyer et al., "Production and Characterization of Recombinant Mouse Brain-Derived Neurotrophic Factor and Rat Neurotrophin-3 Expressed in Insect Cells," *Journal of Neurochemistry* (1994) 62:825-833.

Moody et al., "Synthesis of the Staurosporine Aglycon," *J. Org. Chem.* 57:2105-2114 (1992).

Muid et al., "A novel conformationally restricted protein kinase C inhibitor Ro 31-8425, inhibits human neutrophil . . . post-receptor stimuli," *FEBS* vol. 293, No. 1,2 pp. 169-172 (1991).

Mulqueen et al., "Oral, anti-inflammatory activity of a potent, selective, protein kinase C inhibitor," *Agents Action*, 37:85-89 (1992).

Nabeshima et al., Staurosporine, a protein kinase inhibitor, attenuates basal forebrain-lesion-induced amnesia and cholinergic neuronal deficity, *Neuroscience Letters* (1990) 122:13-16.

Pflug et al., *J. Cell Biochem. Suppl.* 18D Abstract Y215 (1994).

Phelps et al., "Generation Patterns of Four Groups of Cholinergic Neurons in Rat Cervical Spinal Cord: A Combined Tritiated . . . Study", *The Journal of Comparative Neurology* (1988) 273:459-472.

Sarstedt et al., "Reactions with Indole Derivatives, ILVIII," *Heterocycles*, vol. 20, No. 3, pp. 469-476 (1983).

Smith et al., Trophic Effects of Skeletal Muscle Extracts on Ventral Spinal Cord Neurons in Vitro: Separation . . . Proteins with Cholinergic Activity, *The Journal of Cell Biology* (1995) 101:1608-1621.

Toullec et al., "The Bisindolylmaleimide GF 109203X Is a Potent and Selective Inhibitor of Protein Kinase C.," *J. Biol. Chem.* vol. 266, No. 24, pp. 15771-15781 (1991).

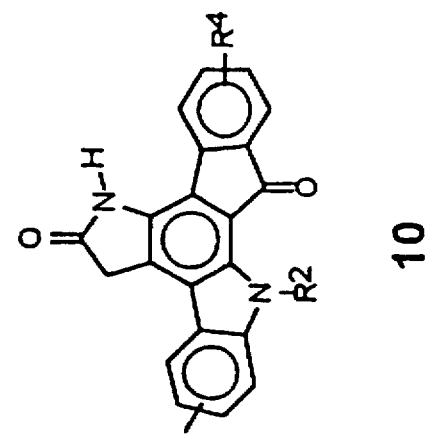
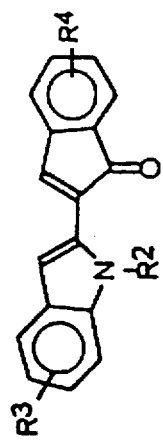
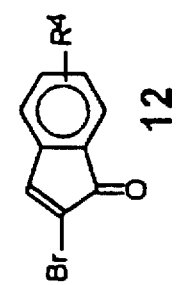
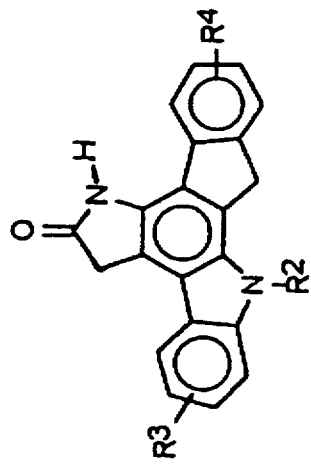
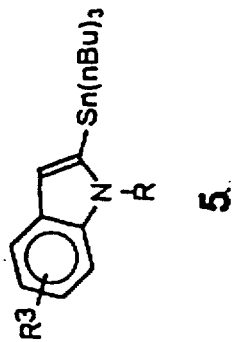
FIG. 6
FIG. 7

FUSED PYRROLO[2,3-C] CARBAZOLE-6-ONES

This is a continuation of application Ser. No. 08/604,474, filed Feb. 21, 1996 now U.S. Pat. No. 5,616,724.

FIELD OF INVENTION

This invention is related to pharmaceutical compounds which are referred to in this patent document as "fused pyrrolo[2,3-c]carbazole-6-ones." Also disclosed are methods for making these compounds, and methods for using the compounds.

BACKGROUND OF THE INVENTION

Human interferon-gamma (IFN-γ) is a natural human immunoregulatory protein. It has been established as an agent effective in the treatment of tumors and virus infections in humans. The precise mechanisms by which IFN-γ inhibits virus and tumor growth in vivo remain unknown. There is evidence that IFN-γ works by at least one of two mechanisms: (1) by acting directly on the virus infected cell and the tumor cell and/or (2) by first activating cells of the immune system which then destroy the virus-infected cell or tumor cell [Interferons and other Regulatory Cytokines, E. De Maeyer and J. De Maeyer-Guignard, John Wiley & Sons, New York (1988)].

One manifestation of a stimulated immune system is the enhanced expression on the surface of immune cells of the proteins of the Major Histocompability Complex (MHC). The MHC is made of class I, II, and III genes that code for the respective class I, II, and III proteins. Class I and II proteins reside on the cell surface and are involved in controlling the immune response, whereas the class III proteins appear in the serum and are not involved in controlling the immune response. Class I and II proteins on antigen presenting cells e.g. monocytes, B lymphocytes, dendritic cells, present foreign antigens to T lymphocytes with subsequent destruction of the cell containing the foreign antigen. The enhanced expression of the class I and II proteins is essential for the immune system to rid an animal of virus-infected cells and enhance specific antibody production. IFN-γ is one of the major regulators of the immune response due to its ability to enhance the expression of MHC class I and II proteins. An example of the benefit of MHC I enhancement by IFN-γ is the enhancement of class I proteins on virus-infected cells. The virus infected cell presents synthesized viral antigens on its cell surface to the T cell receptor on cytotoxic T cells (CD4 cells) with the subsequent destruction of the virus infected cell by the cytotoxic T cell. An example of the benefit of MHC II enhancement by IFNγ is the enhancement of class II proteins on monocytes. Monocytes can ingest invading microorganisms and the class II proteins on the monocyte surface present peptides derived from the invading microorganism. These peptides held by the class II proteins are presented to the T cell receptor on helper T cells (CD8) with subsequent secretion of lymphokines by the CD8 cell. The secreted lymphokines cause proliferation of the antibody synthesizing B lymphocytes which synthesize large amounts of antibody against the invading microorganism.

It can be seem from the above examples that a compound that enhances the IFNγ induction of MHC molecules would be useful in combination with IFN-γ for the treatment of infections by microorganisms. Such a compound might permit a reduction in the dose of IFN-γ, thereby advantageously giving the same therapeutic effect as with IFNγ alone but with fewer of the IFNγ related side effects.

There are at least three reports of compounds that potentiate the IFN-γ-induced MHC expression [Coutinho, G. C., Dudrieu-Trautmann, O., Strosberg, A. D., and Couraud, P. O., Catecholamines Stimulate the IFN-γ-induced Class II MHC Expression on Bovine Brain Capillary Endothelial Cells, J. Immunol., 147, 2525–2529 (1991); Zhu, J., Mix, E., Olsson, T., and Link, H., "Influence of Ion Channel Modulation of in Vitro Interferon-γ Induced MHC Class I and II Expression on Macrophages", Immunopharmacology and Immunotoxicology, 17, 109–136 (1995); Mothes, T., Bendix, U.,, Pfannschmidt, C.,, and Lehmann I., "Effect of Gliadin and Other Food Peptides on Expression of MHC Class II Molecules by HT-29 Cells", Gut, 36, 548–552 (1995)].

SUMMARY OF THE INVENTION

Disclosed herein are a novel class of molecules represented by Formulae I and II, which we refer to as fused pyrrolo[2,3-c]carbazole-6-ones.

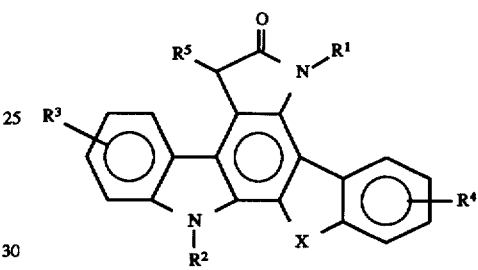

FORMULA I

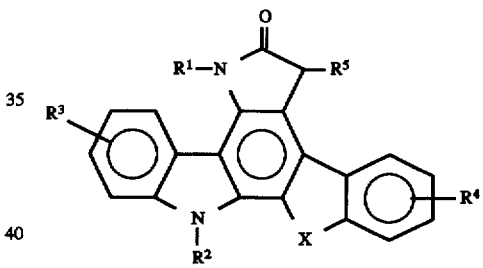

FORMULA II

Constituent numbers are defined, infra. Preferred methods for preparing these compounds are disclosed infra.

We have discovered that our fused pyrrolo[2,3-c]carbazole-6-one compounds (numbering as designated for K-252a and K-252c set forth in Moody et. al, *J. Org. Chem.*, 1992, 57, 2105) potentiate the activity of human IFNγ in inducing the expression of MHC on the surface of receptive cells. The compounds of the invention show ability for enhancing the effectiveness of the immune system, and this in turn provides, beneficially, an enhancement in inhibiting virus and/or tumor growth. We have also discovered that the fused pyrrolo[2,3-c]carbazole-6-one compounds of the invention are useful for potentiating, preferably, neurotrophin-3 (NT-3) activity.

DETAILED DESCRIPTION

We first describe the drawings.

I. BRIEF DESCRIPTION OF DRAWINGS

FIG. 6 is a schematic drawing showing the synthesis of pyrrolo[2,3-c]carbazole-6-ones in which X is C=O from the corresponding compounds in which X is $CH_2$.

FIG. 7 is a schematic drawing showing the synthesis of intermediate 11 to pyrrolo[2,3-c]carbazole-6-ones.

II. Fused pyrrolo[2,3-c]carbazole-6-ones

Figure 1:
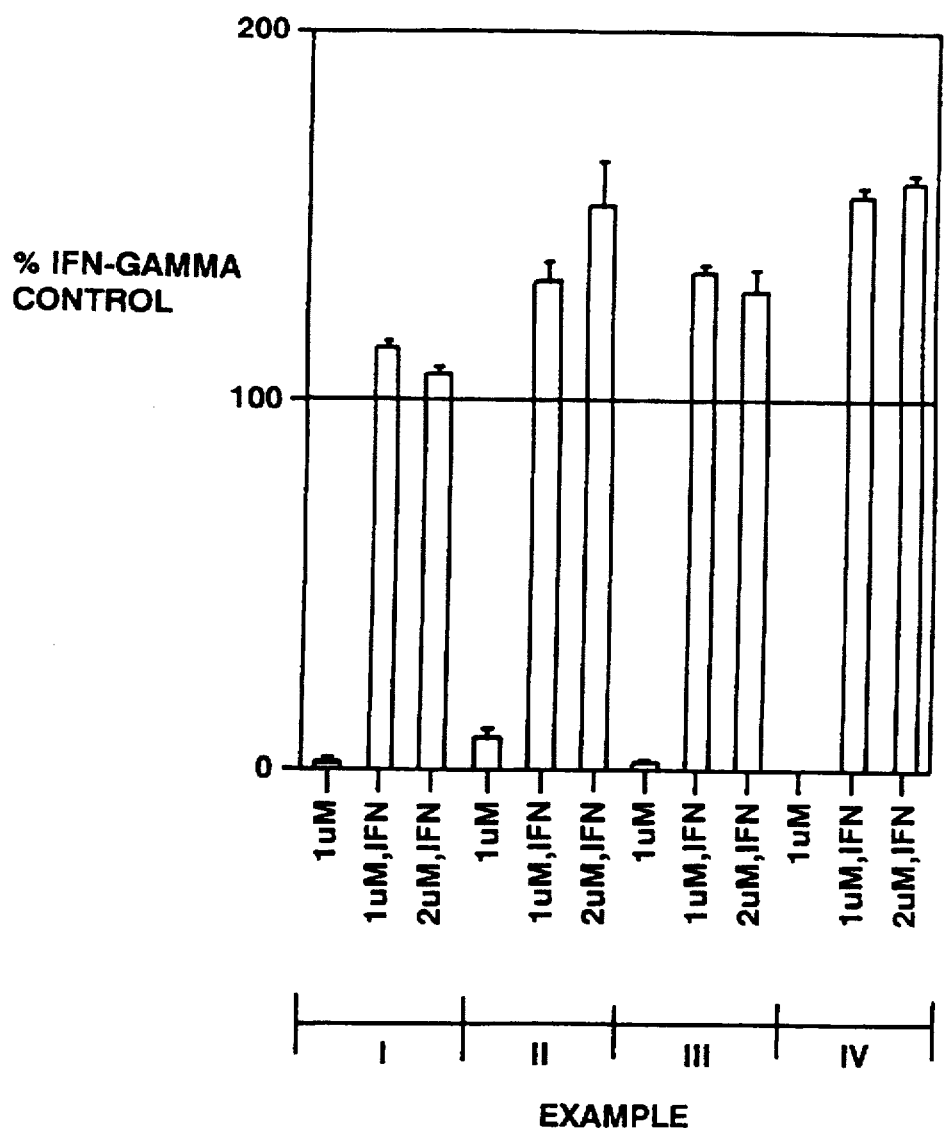
FIG. 1 is a graph showing the enhancement of IFN-γ-induced expression of HLA-DR MHC II molecule by pyrrolo[2,3-c]-carbazole-6-ones of the invention.

The novel compounds of this invention, which are referred to as fused pyrrolo[2,3-c]carbazole-6-one derivatives are represented by the following Formulae:

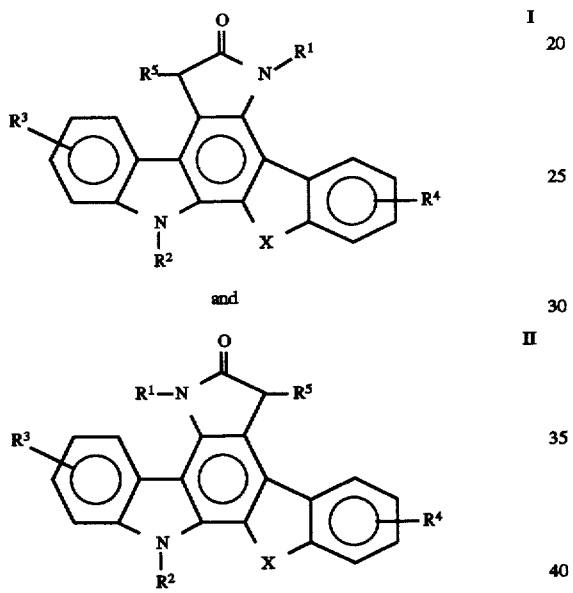

wherein:
a) $R^1$ is selected from the group consisting of H, alkyl of 1–4 carbons, aryl arylalkyl heteroaryl, heteroarylalkyl; C(=O)$R^9$ where $R^9$ is alkyl of 1–4 carbons or aryl; $(CH_2)_nOR^9$, where n is an integer of 1–4; $OR^{10}$, where $R^{10}$ is H or alkyl of 1–4 carbons; $(CH_2)_nOR^{14}$ where $R^{14}$ is the residue of an amino acid after the hydroxyl group of the carboxyl group is removed; $OR^{14}$, $NR^7R^8$; $(CH_2)_nNR^7R^8$, and $O(CH_2)_nNR^7R^8$; and either
 (1) $R^7$ and $R^8$ independently are H or alkyl of 1–4 carbons; or
 (2) $R^7$ and $R^8$ are combined together to form a linking group of the general formula —$(CH_2)_2$—$X^1$—$(CH_2)_2$—, where $X^1$ is O, S or $CH_2$;
b) $R^2$ is selected form the group consisting of H, $SO_2R^9$, $CO_2R^9$, C(=O)$R^9$, alkyl of 1–8 carbons, alkenyl of 1–8 carbons, alkynyl of 1–8 carbons, and a monosaccharide of 5–7 carbons, wherein each hydroxyl group of said monosaccharide is independently selected from the group consisting of unsubstituted hydroxyl and a replacement moiety replacing said hydroxyl group selected from the group consisting of H, alkyl of 1–4 carbons, alkylcarbonyloxy of 2–5 carbons, and alkoxy of 1–4 carbons; wherein either
 1) each alkyl of 1–8 carbons, alkenyl of 1–8 carbons, or alkynyl of 1–8 carbons is unsubstituted; or
 2) each alkyl of 1–8 carbons, alkenyl of 1–8 carbons, or alkynyl of 1–8 carbons independently is substituted with 1–3 groups selected from the group consisting of aryl of 6–10 carbons, heteroaryl, F, Cl, Br, I, CN, $NO_2$, OH, $OR^9$, $O(CH_2)_nNR^7R^8$, $OCOR^9$, $OCONHR^9$, O-tetrahydropyranyl, $NH_2$, $NR^7R^8$, $NR^{10}COR^9$; $NR^{10}CO_2R^9$, $NR^{10}CONR^7R^8$, NHC(=NH)$NH_2$, $NR^{10}SO_2R^9$; S(O)$_yR^{11}$, wherein $R^{11}$ is H, alkyl of 1–4 carbons, aryl of 6–10 carbons, or heteroaryl, and y is 1 or 2; $SR^{11}$, $CO_2R^9$, $CONR^7R^8$, CHO, $COR^9$, $CH_2OR^7$, $CH_2OR^9$, CH=$NNR^{11}R^{12}$, CH=$NOR^{11}$, CH=$NR^9$, CH=NNHCH(N=NH)$NH_2$; $SO_2NR^{12}R^{13}$; wherein either
  (1a) $R^{12}$ and $R^{13}$, independently, are H, alkyl of 1–4 carbons, aryl of 6–10 carbons, or heteroaryl; or
  (2a) $R^{12}$ and $R^{13}$ are combined together to form a —$(CH_2)_2$-$X^1$-$(CH_2)_2$ linking group; PO(OR$^{11})_2$, NHR$^{14}$, NR$^{10}R^{14}$, OR$^{14}$, and a monosaccharide of 5–7 carbons wherein each hydroxyl group of said monosaccharide is independently selected from the group consisting of unsubstituted hydroxyl and a replacement moiety replacing said hydroxyl group selected from the group consisting of H, alkyl of 1–4 carbons, alkylcarbonyloxy of 2–5 carbons, and alkoxy of 1–4 carbons;
c) each $R^3$ and $R^4$, independently, is selected from the group consisting of H, aryl of 6–10 carbons, heteroaryl, F, Cl, Br, I, CN, $CF_3$, $NO_2$, OH, $OR^9$, $O(CH_2)_nNR^7R^8$, $OCOR^9$, $OCONHR^9$, $NH_2$, $(CH_2)_nOR^9$, $(CH_2)_nOR^{10}$, $(CH_2)_nOR^{14}$, $OR^{14}$, $NHR^{14}$, $NR^7R^8$, $NR^7(CH_2)_nNR^7R^8$,$NR^{10}COR^9$, $NR^{10}CONR^7R^8$, $SR^{11}$, S(O)$_yR^{11}$, $CO_2R^9$, $COR^9$, $CONR^7R^8$, CHO, CH=$NOR^{11}$, CH=$NR^9$, CH=$NNR^{11}R^{12}$, $(CH_2)_nSR^9$, $(CH_2)_nS(O)_yR^9$; $CH_2SR^{15}$, where $R^{15}$ is alkyl of 1–4 carbons; $CH_2S(O)_yR^{14}$, $(CH_2)_nNR^7R^8$, $(CH_2)_nNBR^{14}$, alkyl of 1–8 carbons, alkenyl of 1–8 carbons, and alkynyl of 1–8 carbons; and either
 1) each alkyl of 1–8 carbons, alkenyl of 1–8 carbons or alkynyl of 1–8 carbons is unsubstituted; or
 2) each alkyl of 1–8 carbons, alkenyl of 1–8 carbons, or alkynyl of 1–8 carbons is independently substituted as described in b)2) above;
d) $R^5$ is selected from the group consisting of alkyl of 1–8 carbons, alkenyl of 1–8 carbons, and alkynyl of 1–8 carbons; and either
 1) each alkyl, alkenyl, or alkenyl group is unsubstituted; or
 2) each alkyl, alkenyl, or alkynyl group is substituted with 1–3 groups selected from the group consisting of F, Cl, Br, I, CN, $CF_3$, $NO_2$, OH, $OR^9$, $O(CH_2)_nNR^7R^8$, $OCOR^9$, $OCONHR^9$, $NH^2$, $(CH_2)_nOR^9$, $(CH_2)_nOR^{14}$, $NR^7R^8$, $NR^7(CH_2)_nNR^7R^8$, $NR^{10}COR^9$, $NR^{10}CONR^7R^8$, $SR^{11}$, S(O)$_yR^{11}$, $CO_2R^9$, $COR^9$, $CONR^7R^8$, CHO, CH=$NOR^{11}$, CH=$NR^9$, CH=$NNR^{11}R^{12}$, $(CH_2)_nSR^9$, $(CH_2)_nS(O)_yR^9$, $CH_2SR^{15}$, $CH_2S(O)_yR^{14}$, $(CH_2)_nNR^7R^8$, and $(CH_2)_nNHR^{14}$.
e) X is selected from the group consisting of —N—, —O—, —S—, —S(=O)—, —S(=O)$_2$—, alkylene of 1–3 carbons, —C(=O)—, —C($R^2$)=C($R^2$)—, —C($R^2)_2$—, —CH=CH—, —CH(OH)—CH(OH)—, —C(=NOR$^{11}$)—, —C(OR$^{11}$)(R$^{11}$)—, —C(=O)CH(R$^{15}$)—, —CH(R$^{15}$)C(=O)—; —$CH_2$—Z—, —Z—$CH_2$—, —$CH_2ZCH_2$—, where Z is selected from the group consisting of —C(OR$^{11}$)(R$^{11}$)—, O, S, C(=O), and NR$^{11}$; and alkylene of 1–3 carbons substituted with a group selected from the group consisting of one $R^5$ substituent group, $SR^{10}$, $OR^{10}$, $OR^{14}$, $R^{15}$, phenyl, naphthyl, and arylalkyl of 7–14 carbons.

As used herein, the term "aryl" means monocyclic and polycyclic aromatic groups including, for example, phenyl, naphthyl, biphenyl, and xylyl groups. Aryl groups may be unsubstituted or substituted with, for example, alkyl and halogen groups. Halogens include fluorine, chlorine, bromine, and iodine. Preferred are aryl groups which contain 6–10 carbons. Phenyl and naphthyl groups are particularly preferred.

As used herein, the term "heteroaryl" means an aryl moiety which contains at least one basic nitrogen atom and 0–4 heteroatoms selected from O, S, and N. Examples of heteroaryl groups include pyrrolyl, pyranyl thiopyranyl, furyl, imidazolyl, pyridyl, thiazolyl, triazinyl, phthalimido, indolyl, purinyl, and benzothiazolyl.

As used herein with reference to the definition of $R^{14}$, the term "amino acid" means a molecule containing both an amino group and a carboxyl group. It includes an "α-amino acid" which has its usual meaning as a carboxylic acid which bears an amino functionality on the carbon adjacent to the carboxyl group. α-Amino acids can be naturally occurring or non-naturally occurring. Amino acids also include "dipeptides" which are defined herein as two amino acids which are joined in a peptide amide linkage. Thus, constituents of dipeptides are not limited to α-amino acids, and can be any molecule containing both an amino group and a carboxyl group. Preferred are α-amino acids, dipeptides such as lysyl-β-alanine, and aminoalkanoic acids of 2–8 carbons, e.g., 3-dimethylaminobutyric acid.

Preferred "alkyl", "alkenyl", and "alkynyl" groups contain 1–4 carbon atoms.

Preferred $R^1$ groups include H, alkyl of 1–4 carbons, substituted or unsubstituted phenyl, $OR^{10}$, and $O(CH_2)_n NR^7R^8$. Preferred phenyl substituents include alkyl of 1–4 carbons, and halogen. Most preferred is H.

Preferred $R^2$ groups include H, $C(=O)R^9$, alkyl of 1–8 carbons, and alkyl of 1–8 carbons substituted with one $OR^9$, OH, $OCOR^9$, $NR^7R^8$, $NH_2$, $NR^{10}COR^9$, or $NR^{10}R^{14}$ group. Most preferred is H.

Preferred $R^3$ and $R^4$ groups include H, halogen, CN, OH, $OR^9$, $OR^{14}$, $NH_2$, $NR^7R^8$, $(CH_2)_nOR^{10}$, $(CH_2)_nOR^{14}$, $COR^9$, $NR^{10}COR^9$, $NHR^{14}$, and $O(CH_2)_nNR^7R^8$. Most preferred is H.

Preferred $R^5$ groups include H, and alkyl of 1–4 carbons. Most preferred is H.

Preferred X groups include —N—, —O—, —S—, alkylene of 1–3 carbons, —C=O—, —CH$_2$—Z—and —Z—CH$_2$—. Most preferred are —N—, —O—, —S—, and —CH$_2$—groups.

III. Fused Pyrrolo[2,3-c]carbazole-6-one Utilities

Our fused pyrrolo[2,3-c]carbazole-6-ones have evidenced a panoply of important functional activities which find utility in a variety of settings, including both research and therapeutic arenas. For ease of presentation, and in order not to limit the range of utilities for which these compounds can be characterized, the preferred activities of the fused pyrrolo[2,3-c]carbazole-6-ones can be generally described as follows:

A. Enhancement of IFN-γ induction of MHC molecules;
B. Potentiation of function and/or survival of trophic factor responsive cells.

Enhancement of IFN-γ induction of MHC molecules can preferably be established using a human monocyte cell line that responds to IFNγ; a particularly preferred cell line is available from the American Type Culture Collection (ATCC), referred to as THP-1, under accession number ATCC TIB-202. IFN-γ is known to induce expression of the three MHC II heterodimers, HLA-DP, HLA-DQ and HLA-DR; in THP-1 cells. Potentiation of function and/or survival of trophic factor responsive cells, e.g., cells of neuronal lineage, can be preferably established using a cultured spinal cord choline acetyltransferase ("ChAT") assay.

As used herein, the term "potentiation" when used to modify the terms "function" and "survival" means a positive alteration or change. Potentiation which is positive can also be referred to herein as an "enhancement" or "enhancing."

As used herein, the terms "enhance" or "enhancing" or enhancement when used to modify the terms "function" or "survival" or "induction" means that the presence of a fused pyrrolo[2,3-c]carbazole-6-one has a comparatively greater effect on the function and/or survival of a trophic factor responsive cell or, in the case of IFN-γ, induction of MHC molecules, than a comparative cell not presented with the fused pyrrolo[2,3-c]carbazole-6-one.

As used herein the term "neuron," "cell of neuronal lineage" and "neuronal cell" includes, but is not limited to, a heterogeneous population of neuronal types having singular or multiple transmitters and/or singular or multiple functions; preferably, these are cholinergic neurons. As used herein, the phrase "cholinergic neuron" means neurons of the Central Nervous System (CNS) and Peripheral Nervous System (PNS) whose neurotransmitter is acetylcholine; exemplary are basal forebrain and spinal cord neurons.

As used herein a "trophic factor" is a molecule that directly or indirectly affests the survival or function of a trophic factor responsive cell. Exemplary trophic factors include Ciliary Neurotrophic Factor (CNTF), basic Fibroblast Growth Factor (bFGF), insulin and insulin-like growth factors (e.g., IGF-I, IGF-II, IGF-III), interferons, interleukins, cytokines, and the neurotrophins, including Nerve Growth Factor (NGF), Neurotrophin-3 (NT-3), Neurotrophin-4/5 (NT-4/5) and Brain Derived Neurotrophic Factor (BDNF).

A "trophic factor-responsive cell," as defined herein, is a cell which includes a receptor to which a trophic factor can specifically bind; examples include neurons (e.g., cholinergic neurons) and non-neuronal cells (e.g., monocytes and neoplastic cells).

As used herein, "trophic factor activity" and "trophic factor induced activity" are defined as any response which directly or indirectly results from the binding of a trophic factor (e.g., NT-3) to a cell comprising a trophic factor receptor.

As used in the phrases "trophic factor activity" and "trophic factor-induced activity," the term "trophic factor" includes both endogenous and exogenous trophic factors, where "endogenous" refers to a trophic factor already present and "exogenous" refers to a trophic factor added to a system. As defined, "trophic factor induced activity" includes activity induced by (1) endogenous trophic factors; (2) exogenous trophic factors; and (3) a combination of endogenous and exogenous trophic factors.

A. Enhancement of IFNγ Induction of MHC Molecules

The compounds of the invention can be used to enhance IFN-γ induction of MHC molecules. IFN-γ has shown effectiveness in the treatment of virus infections and certain tumors. Due to its dose limiting side effects, however, the utility of IFN-γ has been limited. In an immunocompromised situation, e.g., in a patient evidencing viral infection, enhancement of an IFN-γ mediated immune response would be beneficial, given that IFN-γ induces expression of MHC molecules. Thus, the compounds of this invention which enhance the ability of endogenous IFNγ or exogenously administered IFN-γ to induce MHC expression are of benefit.

As detailed in Section V below, the ability of a fused pyrrolo[2,3-c]carbazole-6-one to enhance IFN-γ induction of MHC molecules is preferably assessed using the THP-1 cell line. This cell line evidences expression of the MHC II heterodimer HLA-DR. Comparing the expression of HLA-DR in the presence of IFN-γ and IFN-γ plus one or more fused pyrrolo[2,3-c]carbazole-6-ones of the present invention provides a rapid and efficient method for determination of enhancement of IFN-γ induction of MHC molecules can be assessed.

The compounds of this invention can be used in the development of in vitro models of enhancement of expression of MHC molecules, function, identification, or for the screening of other synthetic compounds which have activities similar to that of the fused pyrrolo[2,3-c]carbazole-6-ones. The compounds can be utilized in a research environment to investigate, refine and determine molecular targets associated with functional responses. For example, by radiolabelling a fused pyrrolo[2,3-c]carbazole-6-one associated with a specific cellular function (e.g., HLA-DR induction), the target entity to which the fused pyrrolo[2,3-c]carbazole-6-one binds can be identified, isolated, and purified for characterization. In yet another example, a fused pyrrolo[2,3-c]carbazole-6-one can be used as a screening tool to discover agents which have marginal activity, but when combined with at least one disclosed fused pyrrolo[2,3-c]carbazole-6-one are capable of enhancing IFN-γ induction of MHC molecules. Because the disclosed fused pyrrolo[2,3-c]carbazole-6-ones are useful in enhancing IFN-γ induction of MHC molecules, the disclosed compounds beneficially lend themselves to utility as therapeutic agents. Such enhancement is of value in an immunocompromised patient.

B. Potentiation of function and/or survival of trophic factor responsive cells

The fused pyrrolo[2,3-c]carbazole-6-ones of this invention can be used to enhance the function and/or survival of cells of neuronal lineage. The fused pyrrolo[2,3-c]carbazole-6-ones can be utilized individually or with other fused pyrrolo[2,3-c]carbazole-6-ones, or in combination with other beneficial molecules such as indolocarbazoles which also have the ability to potentiate the function and/or survival of a designated cell. In situations where the fused pyrrolo[2,3-c]carbazole-6-one is intended to enhance a biological activity, e.g., neurotrophin activity, exogenous neurotrophins such as NT-3 may be utilized in conjunction with the fused pyrrolo[2,3-c]carbazole-6-one.

A variety of neurological disorders are characterized by neuronal cells which are dying, injured, functionally comprised, undergoing axonal degeneration, at risk of dying, etc. These disorders include, but are not limited to: Alzheimer's; motor neuron disorders (e.g., amyotrophic lateral sclerosis); Parkinson's; cerebrovascular disorders (e.g., multiple sclerosis; peripheral neuropathies (e.g., those affecting DRG neurons in chemotherapy-associated peripheral neuropathy); disorders induced by excitatory amino acids; disorders associated with concussive or penetrating injuries of the brain or spinal cord.

As described in Section V below, the ability of a fused pyrrolo[2,3-c]carbazole-6-one to enhance the function and/ or survival of cells of a neuronal lineage can be determined by employing a basal forebrain ChAT activity assay. ChAT catalyzes the synthesis of the neurotransmitter acetylcholine and is considered an enzymatic marker for a functional cholinergic neuron. A functional neuron is also capable of survival. Enhancement of a neurotrophin such as NT-3 can be determined by comparing the functional activity of the neurotrophin with or without the fused pyrrolo[2,3-c]carbazole-6-one present.

Pharmaceutically acceptable salts of the fused pyrrolo[2, 3-c]carbazole-6-ones also fall within the scope of the present invention. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. Such compositions can be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches.

The composition can be conveniently administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The compounds of this invention can be employed as the sole active agent in a pharmaceutical composition. Alternatively, they can be used in combination with other active ingredients, e.g., synthetic IFN-γ and/or other growth factors which facilitate potentiation of NT-3 such as those disclosed in U.S. Pat. No. 5,468,872 and International Publication No. WO 95/07911 (publication date: Mar. 23, 1995).

The concentrations of the compounds of this invention in a therapeutic composition can vary. The concentration will depend upon factors such as the total dosage of the drug to be administered, the chemical characteristics (e.g., hydrophobicity) of the compounds employed, and the route of administration. The compounds of this invention typically are provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. A preferred dosage of drug to be administered is likely to depend on variables such as the type and extent of progression of the disease or disorder, the overall health status of the particular patient, the relative biological efficacy of the compound selected, and formulation of the compound excipient, and its route of administration.

IV. General Description of the Synthetic Processes

Two synthetic routes were employed to prepare the fused pyrrolo[2,3-c]carbazole-6-one derivatives of the invention. In Method A (FIG. 2) a 2-(aryl) or 2-(heteroaryl)indole derivative (1–4) which is either unsubstituted or substituted at carbons 4–7 (inclusive) of the indole ring ($R^3$) or substituted or unsubstituted in the (hetero)aryl portion ($R^4$) is reacted with maleimide in the presence of a catalyst such as, trifluoroacetic acid (TFA) to give the fused pyrrolocarbazole-6-one derivatives of Formula I (Examples I–IV). Additional Lewis acid catalysts, such as $SnCl_4$, $AlCl_3$, $EtAlCl_2$, or $Et_2AlCl$ may also be used to effect the reaction. The reaction may also be run in a solvent such as TFA, toluene, $CH_2Cl_2$ or 1,2-dichloroethane.

Figure 3:
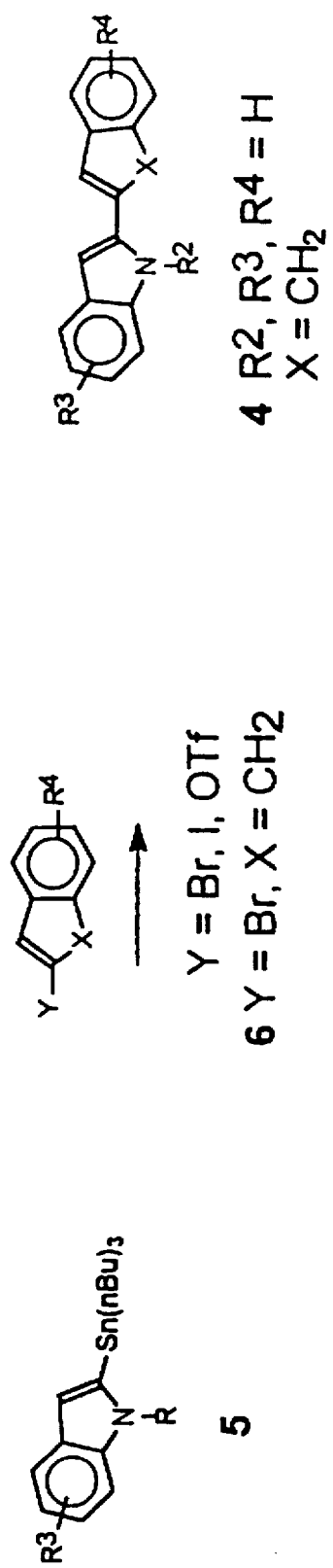
FIG. 3 is a schematic drawing showing the synthesis of intermediates to pyrrolo[2,3-c]carbazole-6-ones.
Figure 4:
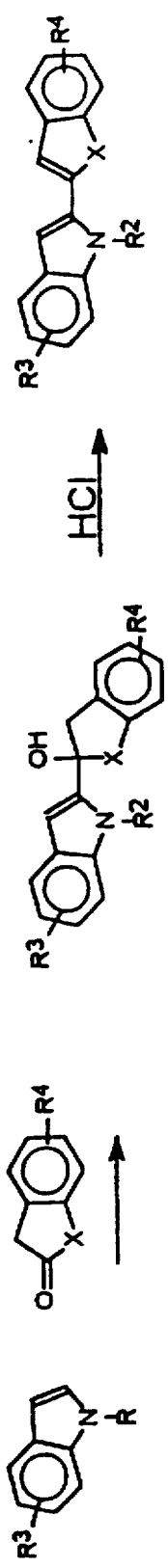
FIG. 4 is a schematic drawing showing an alternate synthesis of intermediates to pyrrolo[2,3-c]carbazole-6-ones.

The bi-aryl indole intermediates, 2,2'-biindole 1 (X=N, $R^2$, $R^3$, $R^4$=H), 2-(2-furyl)indole 2(X=O, $R^2$, $R^3$, $R^4$=H) and 2-(benzothienyl)indole 3 (X=S, $R^2$, $R^3$, $R^4$=H) may be prepared using standard literature procedures (Hudkins, R. L.; et. al *J. Org.Chem.*,1995, 60, 6218) (FIG. 2). 2-(2-Indenyl)indole 4 (FIG. 3) (X=$CH_2$, $R^2$, $R^3$, $R^4$=H), or 2-(2-indenyl)indole derivatives substituted with an $R^3$ or $R^4$ group, may be prepared by reacting 1-carboxy-2-(tributylstannyl)indole 5, or 1-carboxy-2-(tributylstannyl) indole substituted with an $R^3$ group (Hudkins, R. L. et. al *J. Org. Chem.*, 1995, 60, 6218) with 2-bromoindene 6 (*J. Org. Chem.*, 1982, 47, 705) or a 2-bromoindene substituted with an $R^4$ group. Alternatively, 2-(2-indenyl)indole 4 (X=$CH_2$, $R^2$, $R^3$, $R^4$=H), or 2-(2-indenyl)indole derivatives substituted with an $R^3$ or $R^4$ group, may be prepared by reaction of 1H-indole or a derivative thereof containing an $R^3$ group, protected as a lithium indole- 1-carboxylate intermediate (*Tetrahedron Lett.* 26:5935 (1985)), then treated with a strong base, such as t-BuLi then alkylated with an appropriate 2-indanone, or 2-indanone derivative substituted with an $R^4$ group to give the corresponding tertiary alcohol 7 (FIG. 4). The resulting tertiary alcohol 7 is treated with a dilute acid (e.g., 2N HCl in acetone) to give the corresponding 2-(2-indenyl)indole 4 (U.S. Pat. No. 5,475,110). Using other Benzocycloalkan-2-ones such as 2-tetralone in the reaction sequence shown in FIG. 4 will give 2-(2-(3,4-dihydronaphthyl)indole 8 (X=$CH_2CH_2$, $R^2$, $R^3$, $R^4$=H) (U.S. Pat. No. 5,475,110). The palladium-catalyzed cross-coupling methodology (Stille reaction) may be used to prepare other derivatives, for example, where X in FIG. 3 has 1–3 carbons (inclusive), by coupling the 2-(trifluoromethanesulfonate)- or the 2-iodo- or 2-bromovinyl derivative of the corresponding cyclic ketone with 1-carboxy-2-tributylstannylindole to give 2-(2-benzocycloalkenyl)indoles.

The starting 1H-indole derivative described previously is converted to a 1-substituted indole derivative ($R^2$ not H) by standard methodology, for example, by treatment of the 1H-indole with base and an alkylating agent to give a 1-substituted indole. In these examples, the indole derivative can be directly treated with a strong base (e.g., t-BuLi, sec-BuLi, n-BuLi, lithium diisopropylamide) followed by alkylation with a 2-indanone derivative to give the corresponding tertiary alcohol 7, which includes $R^2$ substituents in position one of the indole zing. The 2-(aryl)- or 2-(heteroaryl)indole derivative (1–3), 2-(2-indenyl)indole 4, or 2-(2-(1,2-dihydronaphthyl)indole 8 may be converted to intermediates which contain R2 substituents in position one of the indole ring by the method described above for indole derivatives.

Figure 2:
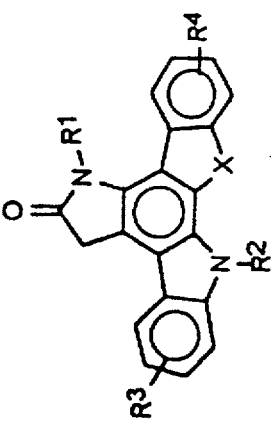
FIG. 2 is a schematic drawing outlining the chemical synthesis of the pyrrolo[2,3-c]carbazole-6-ones of Formula I, Section V (A)–(D).
Figure 2:
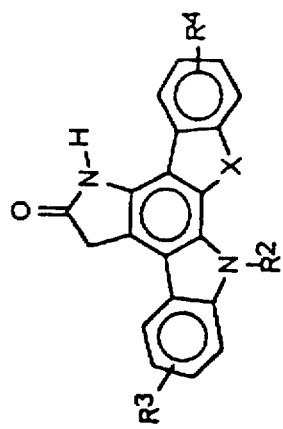
Figure 2:
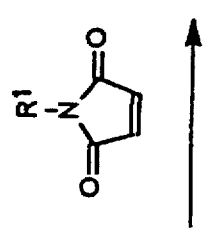
Figure 2:
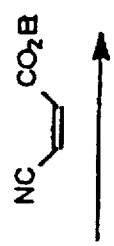
Figure 2:
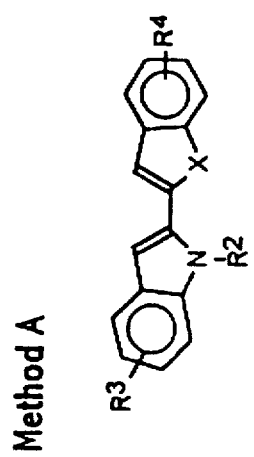
Figure 2:
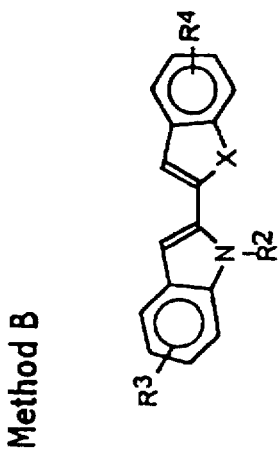

Compounds of general formulae I and II which contain $R^1$ groups, not=H, may be prepared by starting with the appropriate $R^1$ substituted maleimide (FIG. 2, Method A). Compounds of general formulae I and II, in which $R^1$ is hydrogen, can be alkylated in the presence of base (e.g., hydrides, alkoxides, hydroxides of alkali or alkaline earth metals, or of organo-lithium compounds) by treatment with $R^1L$ in which L is a leaving group such as a halogen, mesylate or tosylate to give a fused pyrrolocarbazole-6-one derivative which has an $R^1$ group bound to the lactam nitrogen. Compounds of general formulae I and II, in which $R^5$ is hydrogen, may be converted to derivatives where one or two $R^5$ groups may be added by treatment of a fused pyrrolocarbazole-6-one derivative with one equivalent or an excess of a strong base (e.g., hydrides alkoxides, hydroxides of alkali or alkaline earth metals, or of organo-lithium compounds) with $R^5L$ in which L is a leaving group such as a halogen, or by condensation with an $R^5$ containing ketone or aldehyde carbonyl derivative to give a fused pyrrolocarbazole-6-one derivative which has one or two an $R^5$ groups. The derivatives from the ketone or aldehyde condensation reactions would give vinyl derivatives at $R^5$.

The indole derivatives are prepared using standard methodology (U.S. Pat. No. 3,976,639; U.S. Pat. No. 3,732,245; *The Chemistry of Heterocyclic Compounds*, Indoles Parts One and Two; Houlihan Ed., Wiley-Interscience (1972)). The 2-indanone derivatives can be prepared using previously described procedures (see U.S. Pat. No. 4,192,888; U.S. Pat. No. 4,128.666;*J. Am. Chem. Soc.* 89:4524 (1967); *Tetrahedron Lett.* 43:3789 (1974); *Chem. Ber.* 122:1791 (1989); *Can. J. Chem.* 60:2678 (1982); *Helvetica Chimica Acta* 70:1791 (1987), *Chem. Pharm. Bull.* 33:3336 (1985); *J. Org. Chem.* 55:4835 (1990); *Tetrahedron* 45:1441 (1989); *Synthesis* 818 (1981)).

In Method B (FIG. 2), a 2-(heteroaryl)indole derivative (1–3), or 2-(aryl)indole derivative such as 2-(2indenyl) indole 4 is reacted with ethyl cis-β-cyanoacrylate in the presence of a catalyst such as $SnCl_4$, $AlCl_3$, $EtAlCl_2$, $Et_2AlCl$ or TFA in $CH_2Cl_2$, $C_2H_4Cl_2$ or toluene as solvent to give the 6-oxo carbazole compounds of formula I of the invention.

Figure 5:
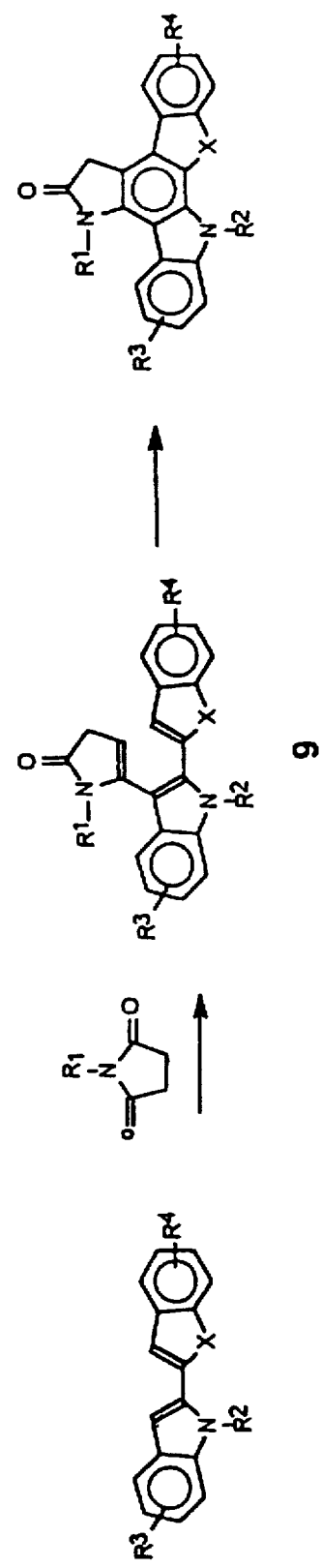
FIG. 5 is a schematic drawing showing the synthesis of pyrrolo[2,3-c]carbazole-6-ones of Formula II.

Compounds of Formula II are prepared as outlined in FIG. 5. Addition of 2-(aryl)-or 2-(heteroaryl)indolylzinc reagents (*Tetrahedron Lett.*, 1994, 35, 793; *Tetrahedron Lett.*, 1994, 35, 7123; *Tetrahedron Lett.*, 1993, 34, 5955; *Tetrahedron Lett.*, 1993, 34, 6245) to succinimide, or an $R^1$ substituted succinimide derivative, via a Reformatzsky type reaction (Synthesis, 1975, 685) followed by dehydration would give compounds of the general structure 9. Palladium catalyzed ring closure (U.S. Pat. No. 5,475,110; *Tetrahedron Lett.*, 1993, 34, 8361) would yield pyrrolo[2,3-c]carbazole compounds of Formula II.

Compounds in which X=(C=O) (general structure 10) are prepared by oxidation of derivatives of general Formula I (or II) where X=$CH_2$, using standard oxidizing reagents (e.g., $SeO_2$, $CrO_3$, $Na_2CrO_7$, or $MnO_2$) (FIG. 6). Alternatively, 2-(2-indenyl)indole 4 may be oxidized to 2-(2-(1-oxoindenyl)indole and used to prepare compounds of Formula I or II where X=(C=O) by the methods shown in FIGS. 2 and 5. Alternatively, 2-(2-(1-oxoindenyl))indole 11 may prepared using the palladium-catalyzed cross-coupling methodology (FIG. 3) by coupling 1-carboxy-2-tributylstannylindole 5 or its derivatives with 2-(trifluoromethanesulfonyl)oxyinden-1-one or 2-bromoinden-1-one 12 (FIG. 7) (*J. Org. Chem.*, 1994, 59, 3453) or one of its derivatives. Compounds of the general structure 10 (X=(C=O)) may undergo a variety of olefination, addition and condensation reactions known to those skilled in the art of organic synthesis to give derivatives, for example, but not limited to, X=(C=C($R^2$)$_2$), C($R^2$)$_2$, C($OR^{11}$)($R^{11}$). Fused pyrrolocarbazole-6-one derivatives where X is S(=O) or S(=O)$_2$ may be prepared by oxidation of X=S derivatives in a manner similar to X=(C=O).

EXAMPLES

V. Specific Description of the Synthetic Processes

The following examples are presented for purposes of illustration and are not to be construed as limiting the scope of the invention in any way.

A. Example I 5H, 7H, 13H-Benzofurano[2,3-a]pyrrolo[2,3-c]
carbazole-6(6H)one (X=O; $R^1$, $R^2$, $R^3$, $R^4$, $R^5$=H)

A mixture of 2-(2-benzofuryl)indole 2 (250 mg; 1.0 mmol) and maleimide (110 mg; 1.2 mmol) in trifluoroacetic acid (2 mL) was heated in a sealed reaction vial at 125° C. for 18 h. The solid precipitated was collected, washed with TFA and dried to give 150 mg (48%) of product. Recrystallization (THF) gave a tan solid; mp>300° C., MS (ES$^+$) 312 (M$^+$), $^1$H NMR (DMSO—d$_6$) δ 4.00 (s, 2H), 4.13 (s, 2H), 7.12 (t, 1H), 7.37 (t, 2H), 7.45 (t, 2H), 7.71 (d, 1H), 7.95 (d, 1H), 8.54 (d, 1H), 10.12 (s, 1H), 11.79 (s, 1H). Anal. calcd for $C_{20}H_{12}N_2O_2$ 0.4 $H_2O$; C, 75.18; H, 4.04; N, 8.77. Found: C, 75.29, H, 3.86, N, 8.60.

B. Example II 5H, 7H, 13H-Benzothieno[2,3-a]pyrrolo[2,3-c]
carbazole-6(6H)one (X=S; $R^1$, $R^2$, $R^3$, $R^4$, $R^5$=H)

A mixture of 2-(2-benzothienyl)indole 3 (100 mg, 0.4 mmol) and maleimide (40 mg; 0.4 mmol) in trifluoroacetic acid (2 mL) was heated in a sealed reaction vial at 125° C. for 16 h. The solid precipitated was collected, washed with cold methanol and dried to give 80 mg (58%) of product. Recrystallization (THF) gave a tan solid; mp>300° C., MS (ES$^+$) 328 (M$^+$), $^1$H NMR (DMSO—d$_6$) δ 4.10 (s, 2H), 7.20 (t, 1H), 7.40–7.60 (m, 4H), 8.10 (d, 1H), 8.80 (m, 1H), 10.86 (s, 1H), 11.80 (s, 1H). Anal. calcd for $C_{20}H_{12}N_2SO$. 0.5 $H_2O$; C, 71.20; H, 3.88; N, 8.30. Found: C, 70.86, H, 3.61, N, 8.39.

C. Example III 5H, 7H, 12H, 13H-Indolo[2,3-a]pyrrolo[2,3-c]
carbazole-6(6H)one (X=N; $R^1$, $R^2$, $R^3$, $R^4$, $R^5$=H)

(1) Method A

To a mixture of 2-2'-biindole 1 (250 mg; 1.0 mmol) and maleimide (110 mg; 1.2 mmol) suspended in toluene (50 mL) was added trifluoroacetic acid (0.5 mL). The solution was heated at reflux for 18 h., cooled to rt, and concentrated to approximately 20 mL. The solution was cooled in an ice bath, the solid precipitate was collected, washed with cold ether and dried to give 150 mg (55%) of product. Purification by column chromatography (EtOAc: hexanes; 2:1) gave a brown-tan solid, mp>320° C., MS (ES$^+$) 311 (M$^+$), $^1$H NMR (DMSO—d$_6$) δ 4.00 (s, 2H), 7.17–7.22 (m, 2H), 7.37–7.42 (m, 2H), 7.67 (d, 2H), 8.03 (d, 1H), 8.58 (d, 1H), 10.87 (s, 1H), 10.92 (s,1H), 11.18 (s, 1H). Anal. calcd for $C_{20}H_{12}N_2O_2$ 0.5 $H_2O$; C, 74.99; H, 4.41; N, 13.12. Found: C, 75.24, H,4.02, N, 13.05.

(2) Method B

A mixture of 2–2'-biindole 1 (100 mg; 0.43 mmol) and ethyl cis-β-cyanoacrylate (50 mg; 0.4 mmol) in methylene chloride (10 mL) was added 25 mL of $SnCl_4$. The mixture was stirred at rt for 30 min. The suspension was cooled on an ice bath, the solid collected, washed with cold ether and dried to give 36 mg (27%) of product. Purification by column chromatography (EtOAc: hexanes; 2:1) gave a brown-tan solid; mp>320° C., MS (ES$^+$) 311 (M$^+$), $^1$H NMR (DMSO—d$_6$) δ 4.00 (s, 2H), 7.17–7.22 (m, 2H), 7.37–7.42 (m, 2H), 7.67 (d, 2H), 8.03 (d, 1H), 8.58 (d, 1H), 10.87 (s, 1H), 10.92 (s,1H), 11.18 (s, 1H). This compound showed identical spectral and analytical characteristics as that prepared by Method A.

D. Example IV 5H, 7H, 12H, 13H-Indeno[2,3-a]pyrrolo[2,3-c]
carbazole-6(6H)one (X=CH$_2$; $R^1$, $R^2$, $R^3$, $R^4$, $R^5$=H)

(1) Method A

A mixture of 2-(2-indenyl)indole 4 (300 mg, 1.3 mmol) and maleimide (160 mg; 1.6 mmol) in trifluoroacetic acid (2 mL) was heated in a sealed reaction vial at 160° C. for 18 h. The solution was evaporated and the solid dissolved in ethyl acetate, then washed with water and dried (MgSO$_4$) to give brown solid product. The crude product was chromatographed (silica gel, EtOac: hexanes; 1:1) to give a product which was treated with THF and filtered. The concentrated residue was triturated with MeOH to give the product; mp 275°–280° C., MS (ES$^+$) 310 (M$^+$), $^1$H NMR (DMSO—d$_6$) δ 4.00 (s, 2H), 4.13 (s. 2H), 7.17 (t, 1H), 7.25–7.42 (m, 3H), 7.50 (d, 1H), 7.71 (d, 1H), 8.00 (d, 1H), 8.37 (d, 1H), 10.75 (s, 1H), 11.33 (s, 1H). IR (KBr) 1650–1700 cm$^{-1}$. Anal. calcd for $C_{21}H_{14}N_2O$ 0.7 $H_2O$; C, 78.10; H 4.81; N, 8.65. Found: C, 78.13, H, 4.41, N, 8.10.

(2) Method B

A mixture of 2-(2-indenyl)indole 4 (75 mg; 0.32 mmol) and ethyl cis-β-cyanoacrylate (81 mg; 0.64 mmol) in trifluoroacetic acid (1 mL) was heated in a sealed reaction vial at 120° C. for 1 h., followed by 4 h at 160° C. The mixture was evaporated at reduced pressure and the residue was triturated with ether. The resulting solid was chromatographed (silica gel; EtOAc: hexanes; 1:1) to give 12 mg (12%) of tan solid product; mp 275°–280° C., MS (ES$^+$) 310 (M$^+$). This compound showed identical spectral data as that prepared in Method A.

E. Example V

Enhancement by Fused Pyrrolo[2,3-c]carbazole-6-ones of the Induction by IFN-γ of the MHC II Antigen HLA-DR A human cell line derived from human monocytes, THP-1 (ATCC TIB 202) that responds to IFN-γ, was used to demonstrate enhancement of HLA-DR by the fused pyrrolo [2,3-c]carbazole-6-ones.

THP-1 cells were grown in RPMI 1640 medium containing 20 uM mercaptoethanol and 10% fetal bovine serum at 37° C. in an atmosphere of 5%CO2:95% air at 100% humidity. For determination of enhancement of HLA-DR by the compounds of the invention, cells were either left untreated as controls, treated with IFN-γ only at 100 units/ml, or treated with compounds of the invention at 1 uM final concentration for 30 min. prior to the addition of IFN-γ at 100 units/ml. Duplicate cultures were used in all experiments. The treated THP-1 cells were incubated at 37° C. for 48 hours and then prepared for analysis of HLA-DR by Flow Cytometry. Induction of HLA-DR was performed by standard procedures as described in *Interferons and Other Regulatory Cytokines*, Edward De Maeyer and Jacqueline De Maeyer Guignard, Chapter 9, John Wiley & Sons, New York. 1988. Cells were prepared for flow cytometry and analyzed for HLA-DR by flow cytometry as instructed in *Current Protocols in Immunology*, Vol. 1, pages 5.0.1–5.8.8, John Wiley & Sons. 1994. One million cells from each treatment were collected by centrifugation and washed twice with phosphate-buffered saline (PBS). The cells were resuspended in 100 ul of PBS containing 10 ug of purified rabbit IgG to block non-specific sites on the cell surface. After 20 min. on ice, 20 ul of anti-HLA-DR monoclonal antibody tagged with the fluorescent label FITC was added and the cells left on ice an additional 30 min to allow the antibody to bind to the HLA-DR. The cells were then washed 2 times with PBS each wash and fixed in 0.5 ml of 0.5% paraformaldehyde. The fixed cells were stored at 4° C. until analyzed by flow cytometry.

The enhancement of HLA-DR by representative fused pyrrolo[2,3-c]carbazole-6-ones is shown in FIG. 1. The enhancement of HLA-DR by IFN-γ alone is designated 100% on the Y axis. There is no significant induction of HLA-DR by the representative compounds alone at 1 uM (FIG. 1). All of the representative compounds enhance the induction of HLA-DR by IFN-γ above the induction by IFN-γ alone, i.e. above 100%. The percent enhancement above IFNγ alone by the four compounds is shown in Table 1. For example, at 2 μM, the compound of Section V(D) (Example IV) enhanced IFN-γ induction of HLA-DR by 60% over IFN-γ alone.

TABLE 1

| Compound of Example # | Conc. of Fused Pyrrolo[2,3-c]carbazole-6-one, uM | Conc. of IFN-γ, Units/ml | Percent Enhancement of HLA-DR |
|---|---|---|---|
| I | — | — | 0 |
| I | — | 100* | 100 |
| I | 1 | 100 | 115 |
| I | 2 | 100 | 108 |
| II | — | — | 0 |
| II | — | 100* | 100 |
| II | 1 | 100 | 133 |
| II | 2 | 100 | 153 |
| III | — | — | 0 |
| III | — | 100* | 100 |
| III | 1 | 100 | 135 |
| III | 2 | 100 | 130 |
| IV | — | — | 0 |
| IV | — | 100* | 100 |
| IV | 1 | 100 | 156 |
| IV | 2 | 100 | 160 |

*IFN-γ alone is defined as 100%.

F. Example VI

NT-3 Potentiation of ChAT Activity in Basal Forebrain Cultures by Pyrrolo[2,3-c]carbazole-6-ones The ability of pyrrolo[2,3-c]carbazole-6-ones to potentiate NT-3 activity in basal forebrain cultures was determined using choline acetyltransferase (ChAT) activity as a measure of cholinergic neuron function or survival. The compounds alone had no effect on ChAT activity. However, in the presence of NT-3, the representative compounds gave a dose dependent potentiation of ChAT activity to levels greater than those elicited by NT-3 alone. The results shown in Table 2 are the result of a single application of NT-3 and the compound to be tested on the day of culture initiation, indicating a prolonged effect on the survival or function of basal forebrain cholinergic neurons. The methods employed are described in U.S. Pat. No. 5,468,872, Columns 18 and 19.

TABLE 2

| Compound of | % Basal (mean ± SD) | | % NT-3 (mean ± SD) | |
|---|---|---|---|---|
| Example # | 100 nM | 300 nM | 100 nM | 300 nM |
| NT-3 + I | 184 ± 3 | 221 ± 2 | 113 ± 2 | 136 ± 1* |
| NT-3 + II | 212 ± 4 | 228 ± 13 | 130 ± 2* | 140 ± 1* |
| NT-3 + III | 180 ± 3 | 203 ± 2 | 114 ± 2 | 129 ± 1* |

NT-3 (100 ng/ml) increased ChAT 163 ± 5% (mean + SD) over control untreated cultures. Test compounds alone had basal (100%) level of activity.
*p < 0.05 statistically significant when compared to NT-3 activity alone by Dunnett t statistics.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention. Documents cited throughout this patent disclosure are hereby incorporated herein by reference.

What is claimed is:

1. A method for enhancing interferon-gamma (IFN-γ) induction of the major histocompatibility (MHC) proteins in a mammalian cell responsive to IFN-γ, said method comprising contacting said cell with an effective amount of a fused pyrrolo[2,3-c]carbazole-6-one represented by a formula selected from the group consisting of:

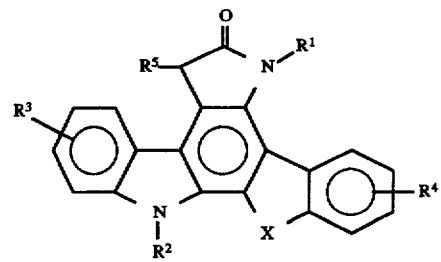

and

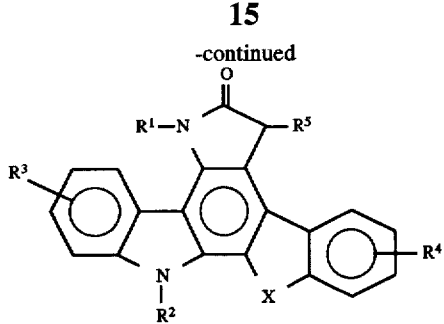

wherein:

a) $R^1$ is selected from the group consisting of H, alkyl of 1–4 carbons, aryl arylalkyl heteroaryl, heteroarylalkyl; $C(=O)R^9$ where $R^9$ is alkyl of 1–4 carbons or aryl; $(CH_2)_nOR^9$, where n is an integer of 1–4; $OR^{10}$, where $R^{10}$ is H or alkyl of 1–4 carbons; $(CH_2)_nOR^{14}$ where $R^{14}$ is the residue of an amino acid after the hydroxyl group of the carboxyl group is removed; $OR^{14}$, $NR^7R^8$; $(CH_2)_nNR^7R^8$, and $O(CH_2)_nNR^7R^8$; and either
  (1) $R^7$ and $R^8$ independently are H or alkyl of 1–4 carbons; or
  (2) $R^7$ and $R^8$ are combined together to form a linking group of the general formula $-(CH_2)_2-X^1-(CH_2)_2-$, where $X^1$ is O, S or $CH_2$;

b) $R^2$ is selected from the group consisting of H, $SO_2R^9$, $CO_2R^9$, $C(=O)R^9$, alkyl of 1–8 carbons, alkenyl of 2–8 carbons, alkynyl of 2–8 carbons, and a monosaccharide of 5–7 carbons, wherein each hydroxyl group of said monosaccharide is independently selected from the group consisting of unsubstituted hydroxyl and a replacement moiety replacing said hydroxyl group selected from the group consisting of H, alkyl of 1–4 carbons, alkylcarbonyloxy of 2–5 carbons, and alkoxy of 1–4 carbons; wherein either
  1) each alkyl of 1–8 carbons, alkenyl of 2–8 carbons, or alkynyl of 2–8 carbons is unsubstituted; or
  2) each alkyl of 1–8 carbons, alkenyl of 2–8 carbons, or alkynyl of 2–8 carbons independently is substituted with 1–3 groups selected from the group consisting of aryl of 6–10 carbons, heteroaryl, F, Cl, Br, I, CN, $NO_2$, OH, $OR^9$, $O(CH_2)_nNR^7R^8$, $OCOR^9$, $OCONHR^9$, O-tetrahydropyranyl, $NH_2$, $NR^7R^8$, $NR^{10}COR^9$; $NR^{10}CO_2R^9$, $NR^{10}CONR^7R^8$, NHC$(=NH)NH_2$, $NR^{10}SO_2R^9$; $S(O)_yR^{11}$, wherein $R^{11}$ is H, alkyl of 1–4 carbons, aryl of 6–10 carbons, or heteroaryl, and y is 1 or 2; $SR^{11}$, $CO_2R^9$, $CONR^7R^8$, CHO, $COR^9$, $CH_2OR^7$, $CH_2OR^9$, $CH=NNR^{11}R^{12}$, $CH=NOR^{11}$, $CH=NR^9$, $CH=NNHCH(N=NH)$ $NH_2$; $SO_2NR^{12}R^{13}$; wherein either
  (1a) $R^{12}$ and $R^{13}$, independently, are H, alkyl of 1–4 carbons, aryl of 6–10 carbons, or heteroaryl; or
  (2a) $R^{12}$ and $R^{13}$ are combined together to form a $-(CH_2)_2-X^1-(CH_2)_2$ linking group; $PO(OR^{11})_2$, $NHR^{14}$, $NR^{10}R^{14}$, $OR^{14}$, and a monosaccharide of 5–7 carbons wherein each hydroxyl group of said monosaccharide is independently selected from the group consisting of unsubstituted hydroxyl and a replacement moiety replacing said hydroxyl group selected from the group consisting of H, alkyl of 1–4 carbons, alkylcarbonyloxy of 2–5 carbons, and alkoxy of 1–4 carbons;

c) each $R^3$ and $R^4$, independently, is selected from the group consisting of H, aryl of 6–10 carbons, heteroaryl, F, Cl, Br, I, CN, $CF_3$, $NO_2$, OH, $OR^9$, $O(CH_2)_nNR^7R^8$, $OCOR^9$, $OCONHR^9$, $NH_2$, $(CH_2)_nOR^9$, $(CH_2)_nOR^{10}$, $(CH_2)_nOR^{14}$, $OR^{14}$, $NHR^{14}$, $NR^7R^8$, $NR^7(CH_2)_n$ $NR^7R^8$, $NR^{10}COR^9$, $NR^{10}CONR^7R^8$, $SR^{11}$, $S(O)_yR^{11}$, $CO_2R^9$, $COR^9$, $CONR^7R^8$, CHO, $CH=NOR^{11}$, $CH=NR^9$, $CH=NNR^{11}R^{12}$, $(CH_2)_nSR^9$, $(CH_2)_nS(O)_y$ $R^9$; $CH_2SR^{15}$, where $R^{15}$ is alkyl of 1–4 carbons; $CH_2S(O)_yR^{14}$, $(CH_2)_nNR^7R^8$, $(CH_2)_nNBR^{14}$, alkyl of 1–8 carbons, alkenyl of 2–8 carbons, and alkynyl of 2–8 carbons; and either
  1) each alkyl of 1–8 carbons, alkenyl of 2–8 carbons or alkynyl of 2–8 carbons is unsubstituted; or
  2) each alkyl of 1–8 carbons, alkenyl of 2–8 carbons, or alkynyl of 2–8 carbons is independently substituted as described in b)2) above;

d) $R^5$ is selected from the group consisting of alkyl of 1–8 carbons, alkenyl of 2–8 carbons, and alkynyl of 2–8 carbons; and either
  1) each alkyl, alkenyl, or alkenyl group is unsubstituted; or
  2) each alkyl, alkenyl, or alkynyl group is substituted with 1–3 groups selected from the group consisting of F, Cl, Br, I, CN, $CF_3$, $NO_2$, OH, $OR^9$, $O(CH_2)_n$ $NR^7R^8$, $OCOR^9$, $OCONHR^9$, $NH^2$, $(CH_2)_nOR^9$, $(CH_2)_nOR^{14}$, $NR^7R^8$, $NR^7(CH_2)_nNR^7R^8$, $NR^{10}COR^9$, $NR^{10}CONR^7R^8$, $SR^{11}$, $S(O)_yR^{11}$, $CO_2R^9$, $COR^9$, $CONR^7R^8$, CHO, $CH=NOR^{11}$, $CH=NR^9$, $CH=NNR^{11}R^{12}$, $(CH_2)_nSR^9$, $(CH_2)_nS$ $(O)_yR^9$, $CH_2SR^{15}$, $CH_2S(O)_yR^{14}$, $(CH_2)_nNR^7R^8$, and $(CH_2)_nNHR^{14}$.

e) X is selected from the group consisting of $-N-$, $-O-$, $-S-$, $-S(=O)-$, $-S(=O)_2-$, alkylene of 1–3 carbons, $-C(=O)-$, $-C(R^2)=C(R^2)-$, $-C(R^2)_2-$, $-CH=CH-$, $-CH(OH)-CH(OH)-$, $-C(=NOR^{11})-$, $-C(OR^{11})(R^{11})-$, $-C(=O)CH$ $(R^{15})-$, $-CH(R^{15})C(=O)-$; $-CH_2-Z-$, $-Z-CH_2-$, $-CH_2ZCH_2-$, where Z is selected from the group consisting of $-C(OR^{11})(R^{11})-$, O, S, $C(=O)$, and $NR^{11}$; and alkylene of 1–3 carbons substituted with a group selected from the group consisting of one $R^5$ substituent group, $SR^{10}$, $OR^{10}$, $OR^{14}$, $R^{15}$, phenyl, naphthyl, and arylalkyl of 7–14 carbons.

thereby causing increased expression of MHC proteins on the surface of said cell.

2. The method of claim 1, wherein said cell is in vitro.

3. The method of claim 2, wherein said cell is a human cell.

4. The method of claim 3, wherein said cell is selected from the group consisting of a monocyte, a B-lymphocyte, and a dendritic cell.

5. The method of claim 4, wherein said cell is a monocyte.

6. The method of claim 2, wherein said MHC proteins include an MHC class I protein or an MHC class II protein.

7. The method of claim 6, wherein said MHC class II protein is selected from the group consisting of HLA-DP, HLA-DQ, and HLA-DR.

8. The method of claim 2, wherein said increased expression of MHC proteins on the surface of said cell enhances an immune system function.

9. The method of claim 2, further comprising the step of contacting said cell with an effective amount of exogenous IFNγ.

10. The method of claim 1, wherein said cell is in vivo.

11. The method of claim 10 wherein said cell is in a human patient.

12. The method of claim 10, wherein said cell is selected from the group consisting of a monocyte, a B-lymphocyte, and a dendritic cell.

13. The method of claim 12, wherein said cell is a monocyte.

14. The method of claim 10, wherein said MHC proteins include an MHC class I protein or an MHC class II protein.

15. The method of claim 14, wherein said MHC class II protein is selected from the group consisting of HLA-DP, HLA-DQ, and HLA-DR.

16. The method of claim 10, wherein said increased expression of MHC proteins on the surface of said cell enhances an immune system function.

17. The method of claim 10, further comprising the step of contacting said cell with an effective amount of exogenous IFN-γ.

18. A method for potentiating the effect of a neurotrophic factor on a mammalian neurotrophic factor-responsive cell, said method comprising contacting said cell with an effective amount of a fused pyrrolo[2,3-c] carbazole-6-one represented by a formula selected from the group consisting of:

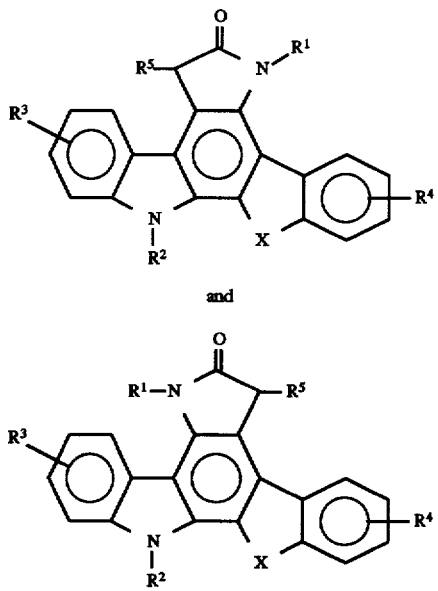

wherein:
a) $R^1$ is selected from the group consisting of H, alkyl of 1–4 carbons, aryl arylalkyl heteroaryl, heteroarylalkyl; C(=O)$R^9$ where $R^9$ is alkyl of 1–4 carbons or aryl; $(CH_2)_nOR^9$, where n is an integer of 1–4; $OR^{10}$, where $R^{10}$ is H or alkyl of 1–4 carbons; $(CH_2)_nOR^{14}$ where $R^{14}$ is the residue of an amino acid after the hydroxyl group of the carboxyl group is removed; $OR^{14}$, $NR^7R^8$; $(CH_2)_nNR^7R^8$, and $O(CH_2)_nNR^7R^8$; and either
  (1) $R^7$ and $R^8$ independently are H or alkyl of 1–4 carbons; or
  (2) $R^7$ and $R^8$ are combined together to form a linking group of the general formula —$(CH_2)_2$—$X^1$—$(CH_2)_2$—, where $X^1$ is O, S or $CH_2$;
b) $R^2$ is selected from the group consisting of H, $SO_2R^9$, $CO_2R^9$, C(=O)$R^9$, alkyl of 1–8 carbons, alkenyl of 2–8 carbons, alkynyl of 2–8 carbons, and a monosaccharide of 5–7 carbons, wherein each hydroxyl group of said monosaccharide is independently selected from the group consisting of unsubstituted hydroxyl and a replacement moiety replacing said hydroxyl group selected from the group consisting of H, alkyl of 1–4 carbons, alkylcarbonyloxy of 2–5 carbons, and alkoxy of 1–4 carbons; wherein either
  1) each alkyl of 1–8 carbons, alkenyl of 2–8 carbons, or alkynyl of 2–8 carbons is unsubstituted; or
  2) each alkyl of 1–8 carbons, alkenyl of 2–8 carbons, or alkynyl of 2–8 carbons independently is substituted with 1–3 groups selected from the group consisting of aryl of 6–10 carbons, heteroaryl, F, Cl, Br, I, CN, $NO_2$, OH, $OR^9$, $O(CH_2)_nNR^7R^8$, $OCOR^9$, $OCONHR^9$, O-tetrahydropyranyl, $NH_2$, $NR^7R^8$, $NR^{10}COR^9$, $NR^{10}CO_2R^9$, $NR^{10}CONR^7R^8$, NHC(=NH)$NH_2$, $NR^{10}SO_2R^9$; S(O)$_yR^{11}$, wherein $R^{11}$ is H, alkyl of 1–4 carbons, aryl of 6–10 carbons, or heteroaryl, and y is 1 or 2; $SR^{11}$, $CO_2R^9$, $CONR^7R^8$, CHO, $COR^9$, $CH_2OR^7$, $CH_2OR^9$, CH=NN$R^{11}R^{12}$, CH=NOR$^{11}$, CH=NR$^9$, CH=NNHCH(N=NH)NH$_2$; $SO_2NR^{12}R^{13}$; wherein either
  (1a) $R^{12}$ and $R^{13}$, independently, are H, alkyl of 1–4 carbons, aryl of 6–10 carbons, or heteroaryl; or
  (2a) $R^{12}$ and $R^{13}$ are combined together to form a —$(CH_2)_2$-$X^1$-$(CH_2)_2$ linking group; PO(O$R^{11}$)$_2$, NH$R^{14}$, N$R^{10}R^{14}$, O$R^{14}$, and a monosaccharide of 5–7 carbons wherein each hydroxyl group of said monosaccharide is independently selected from the group consisting of unsubstituted hydroxyl and a replacement moiety replacing said hydroxyl group selected from the group consisting of H, alkyl of 1–4 carbons, alkylcarbonyloxy of 2–5 carbons, and alkoxy of 1–4 carbons;

c) each $R^3$ and $R^4$, independently, is selected from the group consisting of H, aryl of 6–10 carbons, heteroaryl, F, Cl, Br, I, CN, $CF_3$, $NO_2$, OH, $OR^9$, $O(CH_2)_nNR^7R^8$, $OCOR^9$, $OCONHR^9$, $NH_2$, $(CH_2)_nOR^9$, $(CH_2)_nOR^{10}$, $(CH_2)_nOR^{14}$, $OR^{14}$, $NHR^{14}$, $NR^7R^8$, $NR^7(CH_2)_nNR^7R^8$, $NR^{10}COR^9$, $NR^{10}CONR^7R^8$, $SR^{11}$, S(O)$_yR^{11}$, $CO_2R^9$, $COR^9$, $CONR^7R^8$, CHO, CH=NOR$^{11}$, CH=N$R^9$, CH=NN$R^{11}R^{12}$, $(CH_2)_nSR^9$, $(CH_2)_nS(O)_yR^9$; $CH_2SR^{15}$, where $R^{15}$ is alkyl of 1–4 carbons; $CH_2S(O)_yR^{14}$, $(CH_2)_nNR^7R^8$, $(CH_2)_nNBR^{14}$, alkyl of 1–8 carbons, alkenyl of 2–8 carbons, and alkynyl of 2–8 carbons; and either
  1) each alkyl of 1–8 carbons, alkenyl of 2–8 carbons or alkynyl of 2–8 carbons is unsubstituted; or
  2) each alkyl of 1–8 carbons, alkenyl of 2–8 carbons, or alkynyl of 2–8 carbons is independently substituted as described in b)2) above;

d) $R^5$ is selected from the group consisting of alkyl of 1–8 carbons, alkenyl of 2–8 carbons, and alkynyl of 2–8 carbons; and either
  1) each alkyl, alkenyl, or alkenyl group is unsubstituted; or
  2) each alkyl, alkenyl, or alkynyl group is substituted with 1–3 groups selected from the group consisting of F, Cl, Br, I, CN, $CF_3$, $NO_2$, OH, $OR^9$, $O(CH_2)_nNR^7R^8$, $OCOR^9$, $OCONHR^9$, $NH^2$, $(CH_2)_nOR^9$, $(CH_2)_nOR^{14}$, $NR^7R^8$, $NR^7(CH_2)_nNR^7R^8$, $NR^{10}COR^9$, $NR^{10}CONR^7R^8$, $SR^{11}$, S(O)$_yR^{11}$, $CO_2R^9$, $COR^9$, $CONR^7R^8$, CHO, CH=NOR$^{11}$, CH=N$R^9$, CH=NN$R^{11}R^{12}$, $(CH_2)_nSR^9$, $(CH_2)_nS(O)_yR^9$, $CH_2SR^{15}$, $CH_2S(O)_yR^{14}$, $(CH_2)_nNR^7R^8$, and $(CH_2)_nNHR^{14}$.

e) X is selected from the group consisting of —N—, —O—, —S—, —S(=O)—, —S(=O)$_2$—, alkylene of 1–3 carbons, —C(=O)—, —C($R^2$)=C($R^2$)—, —C($R^2$)$_2$—, —CH=CH—, —CH(OH)—CH(OH)—, —C(=NOR$^{11}$I)—, —C(OR$^{11}$)(R$^{11}$)—, —C(=O)CH(R$^{15}$)—, —CH(R$^{15}$)C(=O)—; —CH$_2$—Z—, —Z—CH$_2$—, —CH$_2$ZCH$_2$—, where Z is selected from the group consisting of —C(OR$^{11}$)(R$^{11}$)—, O, S, C(=O), and NR$^{11}$; and alkylene of 1–3 carbons substituted with a group selected from the group consisting of one $R^5$ substituent group, $SR^{10}$, $OR^{10}$, $OR^{14}$, $R^{15}$, phenyl, naphthyl, and arylalkyl of 7–14 carbons.

thereby causing an effect selected from the group consisting of: enhancing the function of said cell, and enhancing the survival of said cell.

19. The method of claim 18, wherein said cell is in vitro.

20. The method of claim 19, wherein said cell is a human cell.

21. The method of claim 20, wherein said cell selected from the group consisting of: a neuron, a monocyte, a B-lymphocyte, and a neoplastic cell.

22. The method of claim 18, wherein said cell is in vivo.

23. The method of claim 22, wherein said cell is a human cell.

24. The method of claim 23, wherein said cell selected from the group consisting of: a neuron, a monocyte, a B-lymphocyte, and a neoplastic cell.

25. The method of claim 24, wherein said neuron is a cholinergic neuron.

26. The method of claim 18, wherein said trophic factor is selected from the group consisting of: a ciliary neurotrophic factor (CTNF), a basic fibroblast growth factor (bFGF), insulin, an insulin-like growth factor, an interferon, an interleukin, and a neurotrophin.

27. The method of claim 26, wherein said neurotrophin is selected from the group consisting of: neurotrophin 3, neurotrophin-4/5, and brain derived neurotrophic factor (BDNF).

* * * * *